US009233963B2

(12) United States Patent
Song et al.

(10) Patent No.: US 9,233,963 B2
(45) Date of Patent: Jan. 12, 2016

(54) METHOD FOR PREPARING MEROPENEM USING ZINC POWDER

(75) Inventors: Yoon Seok Song, Gunpo (KR); Sung Woo Park, Seoul (KR); Yeon Jung Yoon, Suwon (KR); Hee Kyoon Yoon, Cheongju (KR); Seong Cheol Moon, Yongin (JP); Byung Goo Lee, Suwon (KR); Soo Jin Choi, Yongin (KR); Sun Ah Jun, Yongin (KR)

(73) Assignees: DAEWOONG PHARMACEUTICAL CO., LTD., Kyunggi-Do (KR); DAEWOONG BIO, INC., Gyeonggi-Do (KR)

( * ) Notice: Subject to any disclaimer, the term of this patent is extended or adjusted under 35 U.S.C. 154(b) by 746 days.

(21) Appl. No.: 13/256,178

(22) PCT Filed: Mar. 11, 2010

(86) PCT No.: PCT/KR2010/001516
§ 371 (c)(1),
(2), (4) Date: Nov. 22, 2011

(87) PCT Pub. No.: WO2010/104336
PCT Pub. Date: Sep. 16, 2010

(65) Prior Publication Data
US 2012/0065392 A1 Mar. 15, 2012

(30) Foreign Application Priority Data
Mar. 13, 2009 (KR) .................. 10-2009-0021622

(51) Int. Cl.
*C07D 477/08* (2006.01)
*C07D 477/04* (2006.01)
*C07D 477/10* (2006.01)
*C07D 477/20* (2006.01)

(52) U.S. Cl.
CPC ............ *C07D 477/08* (2013.01); *C07D 477/04* (2013.01); *C07D 477/10* (2013.01); *C07D 477/20* (2013.01)

(58) Field of Classification Search
CPC ...................... C07D 477/20; C07D 487/04
USPC ........................................................ 540/350
See application file for complete search history.

(56) References Cited

U.S. PATENT DOCUMENTS

2010/0240886 A1    9/2010 Nishino et al.

FOREIGN PATENT DOCUMENTS

| EP | 0256377 | 2/1988 |
|----|---------|--------|
| JP | 1990-000714 A | 1/1990 |
| JP | 1995-258258 A | 10/1995 |
| JP | H07258258 A | 10/1995 |
| JP | 2654076 B2 | 9/1997 |
| KR | 10-2006-0020081 | 3/2006 |
| KR | 20070082294 | 8/2007 |
| WO | 2006-035300 | 4/2006 |
| WO | 2007111328 A1 | 10/2007 |

OTHER PUBLICATIONS

Kumagai, Toshio. Heterocycles 1993, 36(8).*
Dowex. The Dow Chemical Company. <http://www.dow.com/products/market/healthcare-and-medical/product-line/amberlite-and-dowex-bioprocessing-resins-and-adsorbents/product/dowex-50wx4/> (1995-2014).*
Sigma-Aldrich. Biological Buffers ,<http://www.sigmaaldrich.com/life-science/core-bioreagents/biological-buffers/learning-center/buffer-reference-center.html>, data originally published in 1986.*
Reichardt, Christian. Solvents and Solvent Effects in Organic Chemistry, 3rd Ed., 2004 471-507.*
Kumagai, T. et al, "Mild and chemoselective cleavage of p-Nitrobenzyl Esters and p-Nitrobenzyl amines with zinc dust", Heterocycles, 1993, 36(8), 1729-1734.
Nagao, et a l., J. Org. Chern. vol. 57,4243-4249 (1992).
Extended European Search Report, EP 10751027.3, Mar. 8, 2012.
Nagao et al. "Beta-Lactams. 3. Asymmetric Total Synthesis of New No-natural 1 Betamethylcarbapenems Exhibiting Strong Antimicrobial Activities and Stability Against Human Renal Dehydropeptidase-I."Joumal of Organic Chemistry, ACS, vol. 57, No. 15, Jan. 1, 1992, p. 4243-4249.

* cited by examiner

*Primary Examiner* — Golam M M Shameem
*Assistant Examiner* — Laura Daniel
(74) *Attorney, Agent, or Firm* — Clark G. Sullivan; Troutman Sanders LLP

(57) ABSTRACT

The present invention relates to an improved method for synthesizing meropenem trihydrate[(1R,5S,6S)-2-[((2'S, 4'S)-2'-dimethylaminocarbozyl)pyrrolidin-4'-ylthio]-6-[(R)-1-hydroxyethyl]-1-methylcarbapen-2-em-3-carboxylic acid, trihydrate], which is a novel carbapenem antibiotic.

17 Claims, No Drawings

METHOD FOR PREPARING MEROPENEM USING ZINC POWDER

TECHNICAL FIELD

The present invention relates to a novel method for preparing meropenem trihydrate which has been recognized as the best antibiotic material of carbapenem, with excellent efficiency and safety. Concretely, the present invention relates to a method for preparing meropenem trihydrate with high purity and yield by conducting a deprotection reaction under a mild reaction condition using zinc powder.

BACKGROUND ART

Meropenem trihydrate (meropenem.$3H_2O$) [Chemical name: (4R,5S,6S)-3-((3S,5S)-5-(dimethylcarbamoyl)pyrrolidin-3-ylthio)-6-((R)-1-hydroxyethyl)-4-methyl-7-oxo-1-azabicyclo[3.2.0]hept-2-ene-2-carboxylic acid, trihydrate] is a compound having the structure of the following formula (1):

[Formula 1]

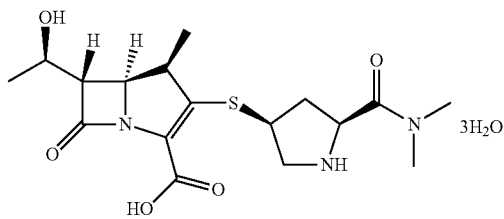

As a prior art regarding a synthesis of meropenem, U.S. Pat. No. 4,943,569 discloses a method for obtaining amorphous meropenem by coupling-reacting MAP with a side chain material as shown in Reaction Scheme 1 below to prepare meropenem-PNB whose carboxylic group is protected by p-methoxybenzyl group or p-nitrobenzyl group, dissolving it in an appropriate amount of a mixture solvent of tetrahydrofuran and ethanol, hydrogenating at room temperature for 3 hours in a buffer solution of morpholinopropanesulfonic acid in the presence of 10% palladium-carbon with 120% of weight ratio, filtering the catalyst, evaporating tetrahydrofuran and ethanol under vacuum, washing the residual solution with ethyl acetate, evaporating the solvent in an aqueous solution under vacuum, isolating by column chromatography using CHP-20P, and freeze-drying.

[Reaction Scheme 1]

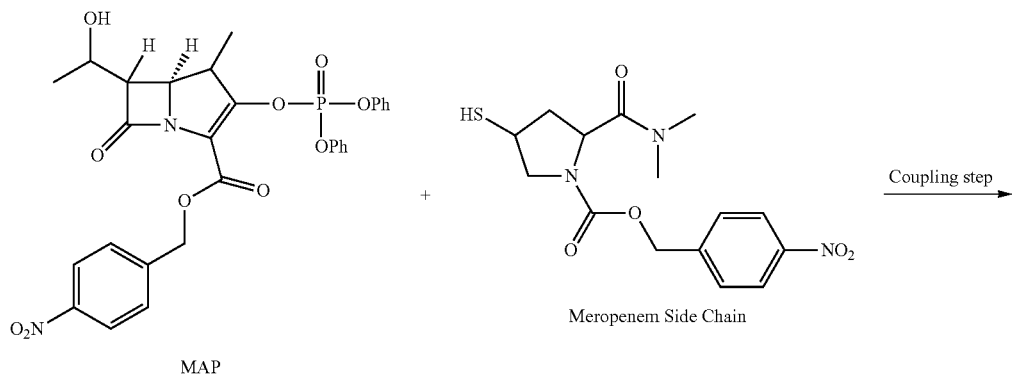

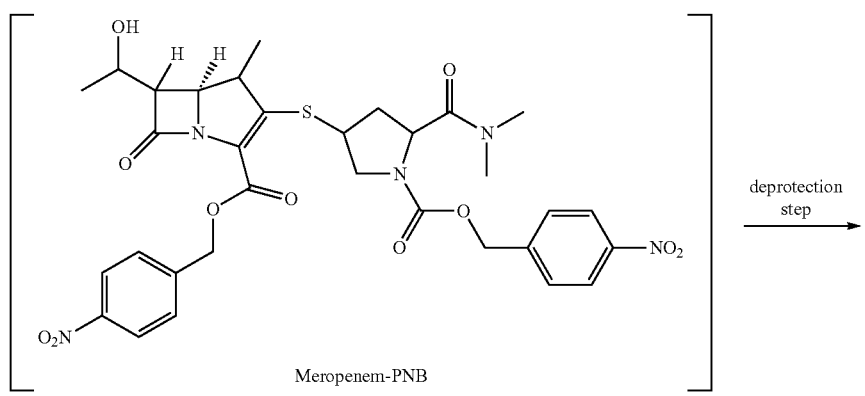

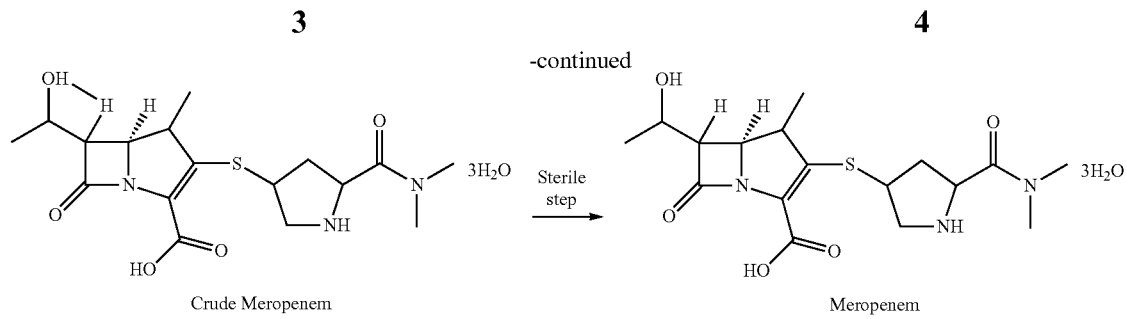

Crude Meropenem → Sterile step → Meropenem

In addition, U.S. Pat. No. 4,888,344 introduces a method for obtaining meropenem trihydrate by dissolving meropenem-PNB in a mixture solvent of tetrahydrofuran (THF) and water, adding 10% palladium-carbon thereto and reacting it under hydrogen atmosphere (4.8 atm) at room temperature for 5 hours, filtering the catalyst, evaporating tetrahydrofuran under vacuum, washing the residual solution with dichloromethane, evaporating the solvent in an aqueous solution under vacuum, concentrating by using reverse osmosis condensing apparatus and crystallizing. As compared with the method of U.S. Pat. No. 4,943,569, since the method of U.S. Pat. No. 4,888,344 does not use a morpholinopropanesulfonic acid buffer solution and conducts the catalyzed hydrogenation reaction in a mixture solvent of water and tetrahydrofuran, it is advantageous that the hydrate can be obtained directly from the aqueous concentrated liquid without using the procedures of column chromatography, freeze-drying, isolation and recovery.

Furthermore, Korean Laid-open Patent Publication No. 1994-14399 improves the yield of the final target compound by introducing a novel process for synthesizing meropenem-PNB which can reduce the production procedures and carry out the production easily, as compared with a conventional method. However, since this method also employs the deprotection procedure of meropenem-PNB of U.S. Pat. No. 4,943,569, a crystallization procedure is further conducted after obtaining meropenem in an amorphous form to obtain more stable trihydrate, resulting in meropenem trihydrate yield of 55.3% (deprotection reaction yield: 69.1%; crystallization yield: 80%).

The above methods have complex processes and use very expensive devices. In particular, they require the expensive palladium-carbon in a large amount. Furthermore, since highly explosive hydrogen gas should be used, they are difficult to industrialize.

CONTENTS OF THE INVENTION

Problems to be Solved

The conventional prior arts for preparing meropenem have the problems explained above. In particular, it is thought that their conditions for removing p-nitrobenzyl group are not appropriate for industrialization. Accordingly, the present inventors have conducted an intensive research to develop a method which is carried out under a milder condition, is easy to apply industrially and has improvements in terms of yield and quality. As a result of such efforts, the present inventors found that such purposes can be achieved by using zinc powder in the deprotection procedure and thus completed the present invention.

Technical Means

Therefore, the present invention provides a method for preparing meropenem trihydrate of formula (1):

[Formula 1]

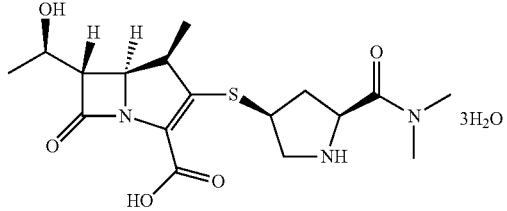

the method being characterized in reacting meropenem-PNB of formula (2) [(4R,5S,6S)-4-nitrobenzyl 3-((3S,5S)-5-(dimethylcarbamoyl)-1-((4-nitrobenzyloxy)carbonyl)pyrrolidin-3-ylthio)-6-((R)-1-hydroxyethyl)-4-methyl-7-oxo-1-azabicyclo[3.2.0]hept-2-ene-2-carboxylate]

[Formula 2]

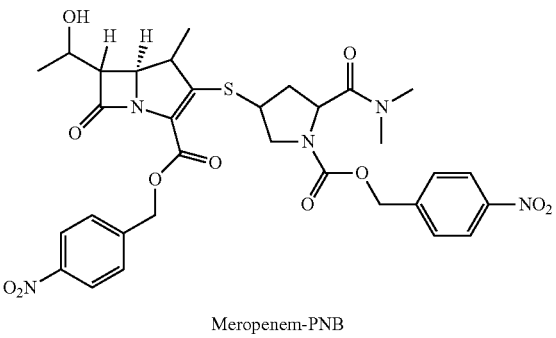

Meropenem-PNB with zinc powder in a mixture solvent of an organic solvent and an aqueous solution of phosphate to remove p-nitrobenzyl group, removing phosphate from the resulting mixture and crystallizing meropenem trihydrate with a mixture solvent for crystallization.

Effect of the Invention

In making up for the problem of prior arts removing p-nitrobenzyl group through a reaction with high-pressure hydrogen, the present invention provides a method that is industrially safe since it utilizes, under a mild condition using zinc powder, the removal of p-nitrobenzyl group which is a protecting group of carboxylic group in carbapenem-type imine (amine) compounds. In addition, the present invention achieves the cost-reduction effect by using cheap ion resins, and the quality-improvement effect by efficiently removing phosphate impurities after the reaction. Furthermore, the present invention provides additional effects of easiness and productivity improvement by in-situ conducting the coupling procedure for synthesizing meropenem-PNB and the deprotection procedure for removing p-nitrobenzyl group.

Concrete Explanation to Carry out the Invention

The procedure for preparing meropenem trihydrate from meropenem-PNB of formula (2) is a deprotection procedure of p-nitrobenzyl group which is a protection group. The reaction is conducted in a mixture solvent of an organic solvent capable of dissolving meropenem-PNB and an aqueous solution of phosphate, at 20 to 50° C. for 0.5 to 5 hours, preferably 1 to 1.5 hours.

The organic solvent capable of dissolving meropenem-PNB is selected from tetrahydrofuran, acetonitrile, acetone, ethyl acetate, methylene chloride, chloroform and the like. To the organic solvent solution of meropenem-PNB, an aqueous solution of phosphate at 0.5 to 1.6M, preferably 1.5M, is added, the temperature is set to about 25° C., and zinc powder is added thereto slowly. The mixing ratio of organic solvent: aqueous solution of phosphate is 5:5 to 15:30, preferably 10:20 by volume per weight of meropenem-PNB. The phosphate may be selected from $KH_2PO_4$, $K_2HPO_4$, $H_3PO_4$, $NaH_2PO_4$ and $Na_2HPO_4$, and $KH_2PO_4$ is preferably used. It is preferable that its concentration becomes a nearly saturated state as the meropenem-PNB solution is added. If the concentration of phosphate is low, the reaction ends with an intermediate in which only the nitro part of protection group is reduced to amine, and thus the target compound cannot be obtained with the maximum yield. If a phosphate buffer solution is used, as compared with the use of phosphate alone, a large amount of impurities is generated due to the considerable decomposition of the target compound, causing the yield and content to decrease. Zinc powder is added in an amount of 4 to 8 times greater than meropenem-PNB on a weight basis. If zinc powder is added portionwise in order to avoid the decomposition of the target compound due to drastic heat generation, the phenomenon of drastic heat generation can be minimized. If the temperature for deprotection reaction is lower than 20° C., the reaction proceeds up to the primarily reduced amine intermediate only, resulting in incompletion of reaction. If the temperature is higher than 50° C., the reaction rate and completion degree increase but the target compound is decomposed in a large amount, resulting in a decrease in yield and purity.

If the reaction is completed, filtration is conducted to remove zinc powder. In the filtration, the zinc powder remaining on the filter is washed with a mixture liquid of water and a polar organic solvent such as tetrahydrofuran, alcohol, etc. to completely isolate the target compound adsorbed to zinc powder in a large amount. The filtrate is then phase-separated, and the aqueous layer is isolated and washed several times with a non-polar organic solvent, e.g., dichloromethane, chloroform, tetrachloromethane, etc.—in order to remove the organic solvent used as a reaction solvent or washing liquid. If the remaining organic solvent is removed by concentration, the target compound is decomposed gradually in the weak acidic reaction solution, which causes a loss in yield and content. Particularly, if hydrophilic organic solvent remains in the aqueous layer during the extraction or concentration procedure, it prevents the target compound from adsorbing to the adsorption resin and lets the target compound elute directly, which causes a loss in yield. Accordingly, its removal is preferable.

The phosphate is removed from the resultant mixture obtained as above.

The first removal of phosphate can be achieved through crystallization. That is, a large amount of phosphate is first removed in crystal form by adding a solvent which dissolves meropenem but not phosphate—for example, a water-miscible solvent such as methanol, ethanol, isopropyl alcohol, tetrahydrofuran, acetone, acetonitrile, etc., preferably methanol.

According to a preferred embodiment of the present invention, after the extraction procedure the aqueous layer containing the target compound is cooled and pre-cooled methanol is added to remove phosphate first. Methanol is added in a total volume of 10 to 80 times greater than meropenem-PNB. At this time, if the temperature in the addition of cooled methanol is too high, a lot of impurities are generated, and thus the addition is preferably done at 20° C. or less. After the addition, phosphate crystals are grown and filtered to be removed.

Preferably, the product after the first removal of phosphate by crystallization and filtration as explained above may be passed through a cationic resin to further remove phosphate.

According to a preferred embodiment of the present invention, when the first removal of phosphate by crystallization and filtration is finished, the aqueous layer containing the target compound is cooled and then passed through a pre-rinsed and pre-cooled cationic resin such as BCMB50, BC108, NM60G, Lewit up 1213, Lewit up 1243, IRC86RF, S8227, etc., preferably BCMB50, to further remove phosphate. That is, the aqueous layer containing the target compound is passed through a cationic resin, by which phosphate is further removed and the target is purified. The pH of the target compound passing through the resin is raised, and the target compound which passed through completely is adjusted to a pH of 5.0 to 7.0, and a buffer solution of 1N-methylmorpholine/acetic acid (pH 6.5 to 7.0) is optionally added and then concentrated to a volume of 3 to 20 times greater than the weight of meropenem-PNB. The buffer solution of 1N-methylmorpholine/acetic acid plays a role of suppressing the decomposition of the target compound during the concentration, thereby increasing the final yield another 5% or higher. During the procedure of concentrating the elutant, the concentration should be done at low temperature in order to minimize the decomposition by heat, and for this the concentration is carried out by using a reverse-osmosis apparatus at low temperature in a short time.

Alternatively, the first removal of phosphate may be conducted by using adsorption resin.

According to another embodiment of the present invention, after the extraction is completed, the aqueous layer containing the target compound is cooled and phosphate is then removed by using a pre-cooled adsorption resin such as SP-207, Amberlite®, XAD4, XAD7, Diaion HP-20, HP-40, etc., preferably SP-207. That is, the aqueous layer containing the target compound is adsorbed to the resin, and water is added thereto in an amount 50 to 100 times greater than the aqueous layer to remove the phosphate used for reaction and highly polar impurities. After the phosphate removal, the target compound is eluted by development with a polar solvent such as methanol, ethanol, isopropyl alcohol, tetrahydrofuran, acetone, acetonitrile, etc., preferably methanol or ethanol, mixed with water at 20 to 80% concentration.

If an aqueous solution containing a polar organic solvent is developed in an adsorption resin, the polarity changes and considerable heat is then generated, by which the target compound may be decomposed. Accordingly, the developing solution to be used should be cooled as much as possible in order to minimize the decomposition of the target compound. The fractions of the elutant containing the target compound are collected, and a buffer solution of 1N-methylmorpholine/acetic acid (pH 6.5 to 7.0) is optionally added and then concentrated to a volume of 3 to 20 times greater than the weight of meropenem-PNB. The buffer solution of 1N-methylmorpholine/acetic acid plays a role in suppressing the decomposition of the target compound during the concentration, thereby increasing the final yield another 5% or higher. During the procedure of concentrating the elutant, the concentration should be done at low temperature in order to minimize the decomposition by heat, and for this the concentration is carried out by using a reverse-osmosis apparatus at low temperature in a short time.

Since the concentrated liquid of the elutant of a cationic resin or adsorption resin as explained above already contains a meropenem-dissolving solvent, a meropenem-undissolving solvent such as acetone, isopropyl alcohol and tetrahydrofuran, preferably acetone, is added thereto in a volume 10 to 110 times greater than the weight of meropenem-PNB, and the crystal is generated at room temperature for 1 hour. The crystal is grown by cooling to 0 to 5° C. and stirring for 2 hours, filtered, washed with acetone, and dried in vacuum at 25° C. In the embodiments of the present invention, as a result of measurement using NMR spectrum, it was confirmed that the target compound synthesized according to the present process was a material equivalent to the USP standard material of meropenem.

According to another embodiment of the present invention, the resultant liquid after the first removal of phosphate can be concentrated to a volume of 3 to 20 times greater than the weight of meropenem-PNB, without passing it through resin. At this time, preferably the buffer solution of methylmorpholine/acetic acid as explained above can be used. In this concentration procedure, the concentration also should be done at low temperature in order to minimize the decomposition by heat, and for this the concentration is carried out by using a reverse-osmosis apparatus at low temperature in a short time. Furthermore, since this concentrated liquid also contains a meropenem-dissolving solvent already, a meropenem-undissolving solvent such as acetone, isopropyl alcohol and tetrahydrofuran, preferably acetone, is added thereto in a volume 10 to 110 times greater than the weight of meropenem-PNB, and the crystal is generated at room temperature for 1 hour. The first crystal of meropenem containing a minor amount of phosphate is grown by cooling to 0 to 5° C. and stirring for 2 hours, filtered, washed with acetone and dried in vacuum at 25° C. Next, the first crystal of meropenem containing phosphate is slurried in a pre-cooled meropenem-low-dissolving solvent such as water to further remove the remaining phosphate. In order to remove the remaining phosphate effectively while minimizing the yield loss of meropenem, the crystal is washed with a cooled mixture solution of isopropanol:water in a volume ratio of 1:2 to 3:1, and the obtained second crystal of meropenem is dried in vacuum at 25° C.

Such a further removal of phosphate through the second crystallization of meropenem can be applied to the crystal of meropenem obtained from the concentrated liquid of the elutant of a cationic resin or adsorption resin as explained above.

Meropenem-PNB of formula (2) used in the present invention can be obtained by a coupling-reaction of MAP of the following formula (3) [(4R,5R,6S)-4-nitrobenzyl 3-(diphenoxyphosphoryloxy)-6-((R)-1-hydroxyethyl)-4-methyl-7-oxo-1-azabicyclo[3.2.0]hept-2-ene-2-carboxylate] and the side chain compound of the following formula (4) [(2S,4S)-4-nitrobenzyl 2-(dimethylcarbamoyl)-4-mercaptopyrrolidin-1-carboxylate].

[Formula 3]

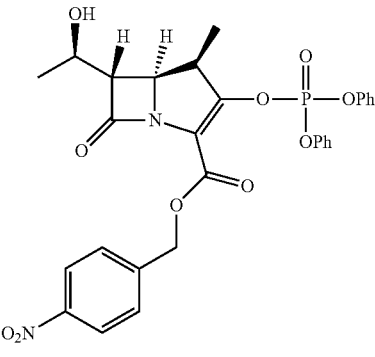

MAP

[Formula 4]

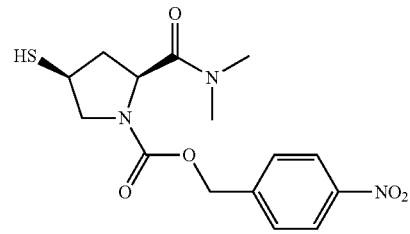

Meropenem Side Chain

In conducting the deprotection step for removing the p-nitrobenzyl group which is a carboxyl-protecting group subsequent to the coupling step for obtaining meropenem-PNB of formula (2), the deprotection step can be conducted after the crystallization of meropenem-PNB after the coupling step, or without the crystallization it can be conducted in situ in the extraction solvent without isolation and purification. Such an in situ procedure is possible because after the coupling procedure, meropenem is dissolved in the aqueous layer and byproducts are dissolved in the organic layer, and thus primary purification is possible only by the extraction procedure. If the deprotection step proceeds in situ, the production time is reduced and the yield is improved, and thus the productivity can be greatly improved.

More concretely, the coupling-reaction of MAP of formula (3) and the side chain compound of formula (4) can be conducted by using a highly polar organic solvent such as dimethylacetamide, dimethylformamide, etc. as the reaction solvent in the presence of a base such as diisopropylethylamine. The reaction is conducted for 1 to 5 hours at −20° C. to room temperature. After the reaction is completed, the reaction solution is extracted with an organic solvent, washed with 0.1 to 6N-HCl, saturated salt water, and treated with anhydrous magnesium sulfate and activated carbon. After filtration, without carrying out the solvent concentration procedure the crystallization is directly conducted in ethyl acetate to synthesize meropenem-PNB. Alternatively, as explained above, without carrying out the crystallization procedure the in situ extraction liquid state can be used in the subsequent deprotection reaction.

In summary, the method according to the present invention has many advantages as follows:

First, it is very economical since cheap zinc powder is used in deprotection reaction, and it is easy to apply industrially without the risk of explosion since the reaction is conducted under a mild condition of ambient temperature and pressure.

Second, conventional methods require very expensive special equipment for the deprotection hydrogen reaction. However, the method according to the present invention can utilize general reaction facilities. In addition, cost reduction effect can be enjoyed since cheap cationic resin can be used, and the reaction scale can be adjusted freely.

Third, the yield loss can be minimized by conducting the deprotection reaction in situ after preparing meropenem-PNB without isolation and purification.

Fourth, since phosphate is removed effectively, the content increases and the quality is improved according to the reduction of impurities.

The present invention is explained in more detail by the following Examples. However, these examples seek to illustrate the present invention only, and the scope of the present invention is not limited by them.

EXAMPLE 1

1-1) Preparation of Meropenem-PNB 20 g of MAP was dissolved in 80 mL of dimethylacetamide, and 12.5 g of the side chain compound was added thereto. After cooling to 0 to 5° C. 6.5 mL of diisopropylethylamine was added dropwise. After stirring at 0 to 5° C. for 5 hours, 120 mL of ethyl acetate and 200 mL of water were added, and the reaction mixture was stirred and then phase-separated. 80 mL of 0.5N HCl was added to the ethyl acetate layer to remove the remaining base, and the resultant mixture was washed with 200 mL of saturated salt water. The remaining water and color were removed by using anhydrous magnesium sulfate and activated carbon. The ethyl acetate solution which was the filtrate was stirred to generate crystal. After stirring at room temperature for 8 hours, cooling to 0 to 5° C. and stirring for 2 hours and filtering, 18.78 g of meropenem-PNB was obtained.

1-2) Preparation of Meropenem Trihydrate 20 g of meropenem-PNB was dissolved in 200 mL of tetrahydrofuran. 60 g of potassium phosphate monobasic ($KH_2PO_4$) dissolved in 400 mL of water was added thereto and heated to 27° C. 80 g of zinc powder was slowly added portionwise and stirred between 25 to 35° C. for 1 hour. After the completion of the reaction was confirmed, 220 mL of methylene chloride was added and stirred for 10 minutes, and then filtered to remove zinc powder. The aqueous layer was separated and washed 2 times with 100 mL of methylene chloride, by which tetrahydrofuran present in the aqueous layer was removed completely. The aqueous layer was cooled and developed in a column filled with adsorption resin SP-207 for adsorption. The resin column was washed with 2 L of water to remove potassium phosphate salt used in the reaction and impurities, and developed with 2 L of 60% methanol to elute meropenem completely. The fractions containing meropenem were collected and a buffer solution of N-methylmorpholine/acetic acid (pH 6.5) was added thereto, and concentration was conducted to a volume 10 times greater than the weight of meropenem-PNB. 1100 mL of acetone was added to generate crystal and stirred at room temperature for 1 hour. After filtration and drying, 9.78 g of meropenem trihydrate was obtained.

$^1$H NMR($CDCl_3$, 400 MHz) δ 5.5 (1H), 5.20 (2H), 4.75 (1H), 4.26 (2H), 3.4~3.8 (4H), 3.3 (2H), 3.0 (6H), 2.62 (1H), 1.2~1.3 (8H)

EXAMPLE 2

Preparation of Meropenem Trihydrate 20 g of meropenem-PNB obtained according to Example 1-1) was dissolved in 200 mL of ethyl acetate. 60 g of potassium phosphate monobasic ($KH_2PO_4$) dissolved in 400 mL of water was added thereto and heated to 30° C. 80 g of zinc powder was added to the solution of ethyl acetate/potassium phosphate monobasic and stirred between 25 to 35° C. for 1 hour. After completion of the reaction, zinc powder was filtered and the filtrate was washed with 60 mL of a mixture solution of tetrahydrofuran/water. The aqueous layer was separated, washed with 200 mL of methylene chloride and developed in a column filled with adsorption resin SP-207 for adsorption. The resin column was washed with 2 L of water to remove potassium phosphate monobasic used in the reaction and impurities, and developed with 2 L of 60% methanol to elute meropenem completely. The fractions containing meropenem were collected, a buffer solution of N-methylmorpholine/acetic acid (pH 6.5) was added thereto, and concentration was conducted to a volume 10 times greater than the weight of meropenem-PNB. 1100 mL of acetone was added to generate crystal and stirred at room temperature for 1 hour. After filtration and drying, 9.66 g of meropenem trihydrate was obtained.

EXAMPLE 3

Preparation of Meropenem Trihydrate 20 g of meropenem-PNB obtained according to Example 1-1) was dissolved in 200 mL of methylene chloride. 60 g of potassium phosphate monobasic ($KH_2PO_4$) dissolved in 400 mL of water was added thereto and heated to 30° C. 80 g of zinc powder was added to the solution of methylene chloride/potassium phosphate monobasic and stirred between 25 to 35° C. for 1 hour. After completion of the reaction, zinc powder was filtered and the filtrate was washed with 60 mL of a mixture solution of tetrahydrofuran/water. The aqueous layer was separated, washed with 200 mL of methylene chloride and developed in a column filled with adsorption resin SP-207 for adsorption. The resin column was washed with 2 L of water to remove potassium phosphate monobasic used in the reaction and impurities, and developed with 2 L of 60% methanol to elute meropenem completely. The fractions containing meropenem were collected, a buffer solution of N-methylmorpholine/acetic acid (pH 6.5) was added thereto, and concentration was conducted to a volume 10 times greater than the weight of meropenem-PNB. 1100 mL of acetone was added to generate crystal and stirred at room temperature for 1 hour. After filtration and drying, 9.84 g of meropenem trihydrate was obtained.

EXAMPLE 4

Synthesis of Meropenem Trihydrate (In Situ Process)

20 g of MAP was dissolved in 80 mL of dimethylacetamide and 12.5 g of the side chain compound was added thereto. After cooling to 0 to 5° C., 6.5 mL of diisopropylethylamine was added dropwise. After stirring for 5 hours, 120 mL of ethyl acetate and 200 mL of water were added and the reaction mixture was stirred and then phase-separated. 80 mL of 0.5N HCl was added to the ethyl acetate layer to remove the remaining base, and the resultant mixture was washed with 200 mL of saturated salt water. The remaining water and color were removed by using anhydrous magnesium sulfate and activated carbon. Without the solvent concentration procedure after filtration, the next step was carried out directly in the state of ethyl acetate solution. 60 g of potassium phosphate monobasic ($KH_2PO_4$) dissolved in 400 mL of water was added to the ethyl acetate solution and heated to 30° C. or higher. 80 g of zinc powder was added thereto and stirred between 25 and 35° C. for 1 hour. After completion of the reaction, zinc powder was filtered and the filtrate was washed with a mixture solution of tetrahydrofuran/water. The aqueous layer was separated, washed 4 times with 100 mL of methylene chloride and developed in a column filled with adsorption resin SP-207 for adsorption. The resin column was washed with 2 L of water to remove potassium phosphate monobasic used in the reaction and impurities, and developed with 2 L of 60% methanol to elute meropenem completely. The fractions containing meropenem were collected, a buffer solution of N-methylmorpholine/acetic acid (pH 6.5) was added thereto, and concentration was conducted to a volume 10 times greater than the weight of meropenem-PNB. 1100 mL of acetone was added to generate crystal and stirred at room temperature for 1 hour. After filtration and drying, 10.30 g of meropenem trihydrate was obtained.

EXAMPLE 5

Preparation of Meropenem Trihydrate 20 g of meropenem-PNB obtained according to Example 1-1) was dissolved in 200 mL of tetrahydrofuran. 400 mL of 1.6M sodium phosphate monobasic ($NaH_2PO_4$) was added thereto and heated to 27° C. 80 g of zinc powder was added slowly and stirred between 25 and 35 t for 1 hour. After completion of the reaction, 220 mL of methylene chloride was added and stirred for 10 minutes, and then filtered to remove zinc powder. The aqueous layer was separated and washed 2 times with 100 mL of methylene chloride, by which tetrahydrofuran present in the aqueous layer was removed completely. The aqueous layer was cooled and developed in a column filled with adsorption resin SP-207 for adsorption. The resin column was washed with 2 L of water to remove sodium phosphate monobasic used in the reaction and impurities, and developed with 2 L of 60% methanol to elute meropenem completely. The fractions containing meropenem were collected and a buffer solution of N-methylmorpholine/acetic acid (pH 6.5) was added thereto, and concentration was conducted to a volume 10 times greater than the weight of meropenem-PNB. 1100 mL of acetone was added to generate crystal and stirred at room temperature for 1 hour. After filtration and drying, 8.53 g of meropenem trihydrate was obtained.

EXAMPLE 6

Preparation of Meropenem Trihydrate 20 g of meropenem-PNB was dissolved in 200 mL of tetrahydrofuran. 60 g of potassium phosphate monobasic ($KH_2PO_4$) dissolved in 400 mL of water was added thereto and heated to 27° C. 80 g of zinc powder was slowly added portionwise and stirred between 25 and 35° C. for 1 hour. After completion of the reaction, zinc powder was removed by filtration. 220 mL of methylene chloride was added and stirred, and the phases were separated. The aqueous layer was isolated and washed 2 times with 100 mL of methylene chloride, by which tetrahydrofuran present in the aqueous layer was removed completely. After the aqueous layer was cooled, 800 mL of cooled methanol was added dropwise to precipitate potassium phosphate crystal. After the crystal was filtered, the filtrate was passed through a column filled with rinsed cationic resin BCMB50 to remove the remaining phosphate. A buffer solution of N-methylmorpholine/acetic acid (pH 6.5) was added thereto, and concentration was conducted to a volume 10 times greater than the weight of meropenem-PNB. 1100 mL of acetone was added to generate crystal and stirred at room temperature for 1 hour. After filtration and drying, 10.15 g of meropenem trihydrate was obtained.

As a result of measurement using NMR spectrum, it was confirmed that the target compound synthesized according to the present Example was a material equivalent to the USP standard material of meropenem.

EXAMPLE 7

Preparation of Meropenem Trihydrate 20 g of meropenem-PNB was dissolved in 200 mL of tetrahydrofuran. 60 g of potassium phosphate monobasic ($KH_2PO_4$) dissolved in 400 mL of water was added thereto and heated to 27° C. 80 g of zinc powder was slowly added portionwise and stirred between 25 and 35° C. for 1 hour. After completion of the reaction, zinc powder was removed by filtration. 220 mL of methylene chloride was added and stirred, and the phases were separated. The aqueous layer was isolated and washed 2 times with 100 mL of methylene chloride, by which tetrahydrofuran present in the aqueous layer was removed completely. After the aqueous layer was cooled, 800 mL of cooled methanol was added dropwise to precipitate potassium phosphate crystal. After the crystal was filtered, the filtrate was concentrated to a volume 10 times greater than the weight of meropenem-PNB. 1100 mL of acetone was added to generate crystal and stirred at room temperature for 1 hour. After filtration, 12.2 g of crystal containing meropenem trihydrate and phosphate was obtained. 12.2 g of this crystal was added to 48 ml of water and stirred for 30 minutes. After filtration and drying, 9.9 g of meropenem trihydrate was obtained.

As a result of measurement using NMR spectrum, it was confirmed that the target compound synthesized according to the present Example was a material equivalent to the USP standard material of meropenem.

The invention claimed is:

1. A method for preparing meropenem trihydrate of formula (1):

[Formula 1]

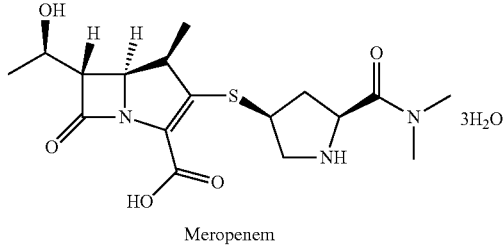

Meropenem comprising:
a. reacting meropenem-PNB of formula (2)

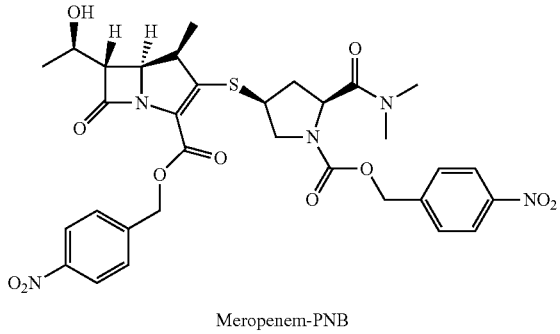

[Formula 2]

Meropenem-PNB with zinc powder in a mixture solvent comprised of an organic solvent and an 0.5 to 1.6 M $KH_2PO_4$ or $NaH_2PO_4$ aqueous solution to remove p-nitrobenzyl from said meropenem-PNB, wherein said mixture solvent does not contain any phosphate other than said potassium phosphate or sodium phosphate;
b. removing phosphate from the mixture resulting from step a; and
c. crystallizing meropenem trihydrate by the addition of a crystallization solvent.

2. The method of claim 1, wherein said zinc powder to meropenem-PNB are present in step a at a weight ratio of from 4:1 to 8:1.

3. The method of claim 1, wherein the organic solvent is selected from tetrahydrofuran, acetonitrile, acetone, ethyl acetate, methylene chloride and chloroform.

4. The method of claim 1, wherein the reaction in step a is conducted at a temperature of 20 to 50° C. for 0.5 to 5 hours.

5. The method of claim 1, wherein after the removal of p-nitrobenzyl group, the resulting mixture is purified by a resin column and concentrated, and then crystallized in a crystallization solvent comprising a meropenem-undissolving solvent.

6. The method of claim 5, wherein the crystallization solvent is selected from acetone, isopropyl alcohol and tetrahydrofuran.

7. The method of claim 5, wherein said resin column is an adsorption resin column.

8. The method of claim 5, wherein said resin column comprises water and a polar elution solvent selected from methanol, ethanol, isopropyl alcohol, acetone, acetonitrile and tetrahydrofuran.

9. The method of claim 5, comprising concentrating the elutant from the column to a volume of 3 to 20 times greater than the weight of meropenem-PNB, wherein said crystallization solvent is added at a weight of 10 to 110 times greater than the weight of meropenem-PNB.

10. The method of claim 1, further comprising preparing meropenem-PNB of formula (2) by a coupling-reaction of MAP of formula (3) and the side chain compound of formula (4):

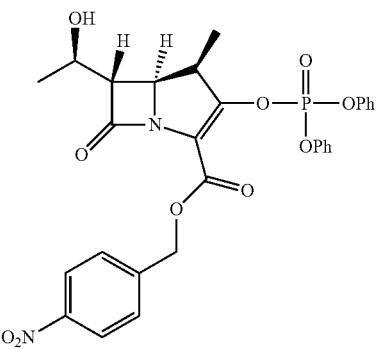

[Formula 3]

MAP

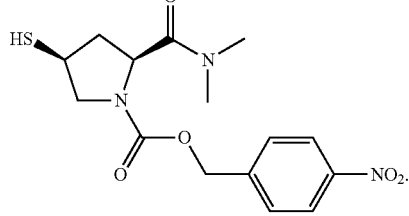

[Formula 4]

Meropenem Side Chain

11. The method of claim 10, wherein said meropenem-PNB prepared by the coupling reaction is used in step a of claim 1 without prior crystallization.

12. The method of claim 1, wherein said phosphate is removed step b through crystallization in a solvent which dissolves meropenem but not phosphate, thereby forming a crystallized phosphate, and filtering said crystallized phosphate from said solvent.

13. The method of claim 12, wherein the solvent which dissolves meropenem but not phosphate is methanol.

14. The method of claim 12, further comprising passing said solvent through cationic resin.

15. The method of claim 12, further comprising crystallizing meropenem trihydrate from said solvent.

16. The method of claim 15, wherein the crystallization of meropenem trihydrate is conducted using a crystallization solvent selected from acetone, isopropyl alcohol and tetrahydrofuran.

17. The method of claim 15, wherein the meropenem trihydrate is slurried in water to further remove phosphate.

* * * * *